United States Patent [19]

Hunter et al.

[11] Patent Number: 5,326,781
[45] Date of Patent: Jul. 5, 1994

[54] MEDICAMENTS

[75] Inventors: Ann J. Hunter, Harlow; Rodney C. Young, Hertford; Lars M. Wood, London, all of England

[73] Assignee: Smith Kline & French Laboratories Limited, Welwyn Garden City, England

[21] Appl. No.: 946,366
[22] PCT Filed: May 7, 1991
[86] PCT No.: PCT/GB91/00724
§ 371 Date: Jan. 8, 1993
§ 102(e) Date: Jan. 8, 1993
[87] PCT Pub. No.: WO91/16890
PCT Pub. Date: Nov. 14, 1991

[30] Foreign Application Priority Data

May 9, 1990 [GB] United Kingdom ............. 9010366.4

[51] Int. Cl.$^5$ ............................................. A01N 43/38
[52] U.S. Cl. ............................................................ 514/410
[58] Field of Search ...................... 514/410, 310, 404

[56] References Cited

U.S. PATENT DOCUMENTS 4,234,594 11/1980 Winn et al. ..................... 514/310 X
4,767,775 8/1988 Jelich et al. ..................... 514/404 X
5,049,563 9/1991 Haeck et al. ..................... 514/410 X

FOREIGN PATENT DOCUMENTS 0125033 11/1984 European Pat. Off. .
0125783 11/1984 European Pat. Off. .

OTHER PUBLICATIONS

Kruse et al, "Some Benzyl-substituted Imidazoles . . . Copper Binding Site", J. Med. Chem., vol. 33, pp. 781–789, Feb., 1990.

Primary Examiner—Arthur C. Prescott
Attorney, Agent, or Firm—Mary E. McCarthy; Stephen Venetianer; Edward T. Lentz

[57] ABSTRACT

Benzylimidazole derivatives are described as anxiolytic agents.

3 Claims, No Drawings

MEDICAMENTS

The present invention relates to the use of imidazole derivatives in the manufacture of medicaments having anxiolytic and nootropic activities and a method of treating anxiety or cognitive disorders by administering them.

EP-A-125033 and EP-A-125783 disclose imidazole derivatives as dopamine-$\beta$-hydroxylase (DBH) inhibitors having utility as diuretic, natriuretic, cardiotonic, antihypertensive, vasodilator, anti-ulcerogenic or anti-parkinson disease agents. 1-Benzyl-2-(hydroxymethyl)imidazole has previously been disclosed for example in U.S. Pat. No. 4,746,669 as an intermediate in the synthesis of immunoregulants. There has been no suggestion of any pharmacological activity for this compound.

It has now been discovered that 1-benzyl-2-(hydroxymethyl)imidazole and certain of the imidazole compounds disclosed in the above-noted European patent applications surprisingly have anxiolytic and nootropic activities.

Accordingly the present invention provides the use of a compound of the formula (1):

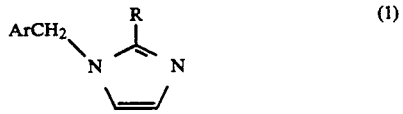

wherein
Ar is 3,5-difluorophenyl, 2,6-dichlorophenyl, 3,4-dihydroxyphenyl, or 3-fluoro-4-methoxyphenyl and
R is SH, or
Ar is phenyl and R is $CH_2NH_2$ or $CH_2OH$,
or a pharmaceutically acceptable salt thereof, in the manufacture of a medicament having anxiolytic and/or nootropic activity.

In another aspect this invention provides a method of treating anxiety and/or cognitive disorders in a host in need thereof which comprises administering an effective amount of a compound of the formula (I) as hereinbefore defined or a pharmaceutically acceptable salt thereof.

Particular compounds of the formula (1) are: 1-benzyl-2-(hydroxymethyl)imidazole, 1-benzyl-2-(aminomethyl)imidazole, and pharmaceutically acceptable salts thereof.

In another aspect this invention provides 1-benzyl-2-(hydroxymethyl)imidazole or a pharmaceutically acceptable salt thereof for use as a medicament.

Suitable pharmaceutically acceptable salts can be formed with hydrochloric, hydrobromic, sulphuric, phosphoric, nitric, acetic, citric, tartaric, maleic, lactic, ascorbic, fumaric, oxalic, methanesulphonic and ethanesulphonic acids.

In order to use a compound of this invention or a pharmaceutically acceptable salt thereof for the treatment of humans and other mammals it is normally formulated in accordance with standard pharmaceutical practice as a pharmaceutical composition.

Compounds of this invention and their pharmaceutically acceptable salts can be administered in standard manner for example orally, sublingually, parenterally, transdermally, rectally, via inhalation or via buccal administration.

Compounds of this invention and their pharmaceutically acceptable salts which are active when given orally or via buccal administration can be formulated appropriately in dosage forms such as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations can be used. Examples of such carriers include magnesium stearate, starch, celluloses, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions can be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil or solubilising agent, for example polyethylene glycol, polyvinylpyrrolidone, 2-pyrrolidone, cyclodextrin, lecithin, arachis oil, or sesame oil.

A typical suppository formulation comprises a compound of this invention or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/kg to 10 mg/kg, and preferably from 0.005 mg/kg to 5 mg/kg, and each dosage unit for parenteral administration contains suitably from 0.001 mg/kg to 5 mg/kg, of a compound of the formula (1) or a pharmaceutically acceptable salt thereof calculated as the free base.

The daily dosage regimen for oral administration is suitably about 0.00l mg/kg to 40 mg/kg, preferably 0.005 mg/kg to 20 mg/kg, of a compound of the formula (I) or a pharmaceutically acceptable salt thereof calculated as the free base. The daily dosage regimen for parenteral administration is suitably about 0.001 mg/kg to 20 mg/kg of a compound of the formula (1) or a pharmaceutically acceptable salt thereof calculated as the free base. The active ingredient may be administered as required for example from 1 to 4 times a day or by infusion. For administration by inhalation dosages are controlled by a valve, are administered as required and for an adult are conveniently in the range 0.05–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of this invention are anti-convulsants such as phenytoin, anti-depressants such as amitriptyline, anxiolytics such as diazepam, nootropics such as oxiracetam or acetylcholinesterase inhibitors such as tetrahydroaminoacridine.

The anxiolytic and nootropic activities of the compounds of this invention were assessed in the following experiments.

EXPERIMENT 1

Activity of 1-[3′,5′-Difluorobenzyl]-2-mercaptoimidazole on Anxiety in a Simple Mouse Model Using a Black and White Test Box Situation Methods Naive male albino BKW mice, 25–30 g, were used in all experiments. The mice were kept on a 12 hour light and 12 hour dark cycle with lights off at 8.00 am and on at 8.00 pm.

The apparatus used for the detection of changes in anxiety consisted of an open topped box (45×27×27 cm high) one-third painted black and illuminated under a dim red light (1×60 W) and partitioned from the remainder of the box which was painted white and brightly illuminated with a 100 W light source located 17 cm above the box. Access between these areas was enabled by means of a 7.5×7.5 cm opening located at floor level at the centre of the partition. The floor areas was lined into 9 cm squares. The test was conducted between 13.00 and 18.00 hours in a quiet, darkened room illuminated with red light only. Animals were thus taken in a dark container from a dark holding room to the dark testing room..

Animals that had received drug or vehicle injections were placed individually into the centre of the white area and their behaviour observed over a 5 minute period by remote video recording. Four behavioural parameters were noted, the number of exploratory rears in the black and white sections, the number of line crossings in the black and white sections, the percentage of time spent in the black section, and the latency of the first move from the white to the black compartment. Experimenters remained blind to drug treatment throughout, with the code only being broken after analysis was complete.

Results

Animals taken from the dark and placed in a brightly lit area showed aversion to the light. This aversion was reduced by anxiolytic agents. Thus, diazepam treatment leads to increased activity in the white area (both rearings and line crossings) associated with decreased activity in the black area: the overall activity of the animals remained unchanged, and was simply redistributed in preference of the white area. Latency to move to the black was delayed, and percentage time spent in the black was reduced. Identical profiles of behavioural change have been obtained using other benzodiazepine compounds. In contrast, general depressant agents such as haloperidol cause general depression in both the black and white sections whilst amphetamine causes an anxiogenesis with decreased activity in the white correspondingly associated with increased activity (rearings and line crossings) in the black section.

Similarly to diazepam, treatment with 1-[3′,5′-difluorobenzyl]-2-mercaptoimidazole leads to increased activity in the white section of the box (expressed as rearings and line crossings), with decreased activity in the black, seen not only as reduced rears and crossings but also as reduced percentage time spent in the black. As with diazepam treatment, animals given 1-[3′,5′-difluorobenzyl]-2-mercaptoimidazole showed a delayed latency to move to the black.

Conclusions

1-[3′,5′-Difluorobenzyl]-2-mercaptoimidazole exhibits an anxiolytic profile of action similar to that seen when mice are treated with a known anxiolytic agent such as a diazepam. The two agents were approximately equieffective, with an effective dose range of 0.01 to 10 mg/kg for 1-[3′,5′-difluorobenzyl]-2-mercaptoimidazole and 0.125 to 1 mg/kg for diazepam. Higher doses of diazepam caused sedation which reduced overall behaviour in the test. This problem was not encountered with the use of 1-[3′,5′-difluorobenzyl]-2-mercaptoimidazole. These results demonstrate the anxiolytic activity of 1-[3′,5′-difluorobenzyl]-2-mercaptoimidazole.

EXPERIMENT 2

Activity of 1-3′,5′-Difluorobenzyl]-2-Mercaptoimidazole on Cognitive Performance of Mice Assessed Using a Simple Habituation Test and Scopolamine Challenge Methods The method used animals and approaches as described in Experiment 1. However, whilst naive mice were used in all tests described in Experiment 1, in the studies on habituation mice were placed repeatedly in the black:white box (daily for 7 days). During the 8 days of exposure to the box mice 'learn' rapidly to avoid the white, averse area. This reflects in reduced latency to move to the black, and increased behaviour and time spent in the black.

Because of the nature of the test procedure used it was essential to use 1-[3′,5′-difluorobenzyl]-2-mercaptoimidazole at a subanxiolytic dose of 1 μg/kg i.p., given once daily throughout the 7 day test period. On day 6 (habituation established) mice received an acute challenge with scopolamine 40 minutes before test. This disorientates animal behaviour and disturbs the habituation process: the animals do not show overt peripheral cholinergic problems at this dose of scopolamine, pupil diameter is normal, and tape analysis shows that animals can easily locate the door to the black compartment: the problem appears to be an association of the black compartment with escape from a more aversive compartment. The basal habituation curve is not modified by arecoline given at doses up to 30 mg/kg/day by intraperitoneal infusion (to maintain constant blood levels and reduce peripheral side effects). However, this treatment with arecoline does inhibit the scopolamine impairment.

Results

Daily treatment with 1-[3',5'-difluorobenzyl]-2-mercaptoimidazole was shown to improve basal learning of mice in the habituation test. This was seen as increased speed of learning to avoid the white (rears in the white area were significantly reduced on days 3 to 5, and a corresponding increase in activity in the black area and a speeding of the habituation process was also observed). The same picture of enhanced habituation was observed on measures of line crossings, in percentage of time spent in the black area and in the speed (latency) with which animals learn to move from the white to the black compartment.

On all measures of habituation the impairments caused by challenge with 0.25 mg/kg i.p. scopolamine (not mimicked by methyl scopolamine) were antagonised by the treatment with 1-[3',5'-difluorobenzyl]-2-mercaptoimidazole.

Conclusions

1-[3',5'-Difluorobenzyl]-2-mercaptoimidazole is shown to improve basal habituation in mice and to inhibit the impairments in habituation patterns caused by scopolamine challenge. This indicates that 1-[3',5'-difluorobenzyl]-2-mercaptoimidazole has nootropic activity and is capable of improving basal performance as well as impaired performance linked with a cholinergic deficit. The combination of anxiolytic and nootropic activities is particularly beneficial since humans work more effectively when less anxious. By contrast existing anxiolytic agents such as benzodiazepines are known to cause moderate to severe cognitive impairments.

Compounds having nootropic activity are useful in restoring learning and treating memory difficulties associated with ageing. They have utility in the treatment of dyslexia and dementia associated with various pathologies such as Alzheimer's disease, post-stroke syndrome and multi-infarct dementia.

EXPERIMENT 3

Activity of Compounds of Formula (1) on Anxiety in the Elevated Plus Maze

Methods

The apparatus used for this experiment consisted of an elevated maze made up of two open arms and two closed arms. Control animals spend most of their time in the closed arms, whereas treatment with anxiolytics, e.g. diazepam, increases the time spent in the open arms.

Lister hooded rats (250–350 g) were dosed at nine minute intervals and placed in a cage different from their home cage. Thirty minutes later the rats were placed in the centre of the maze, facing one of the open arms, and monitored for five minutes.

During this five minutes the number of crossings made by the rat over each of the lines and the amount of time spent in the closed and open arms was noted. After testing the animal was replaced in its home cage, the maze cleaned, another rat dosed and the next rat placed on the maze.

Results

Treatment with the known anxiolytic agent (1.5 mg/kg) diazepam increased the percentage time spent in the the open arms. This was also true for for the compounds of the formula (1) (0.1 and 1.0 mg/kg):

| No. | Ar | R | % Anxiolytic Activity Relative to Diazepam |
| --- | --- | --- | --- |
| 1 | 3,5-difluorophenyl | SH | 100 |
| 2 | 3,4-dihydroxyphenyl | SH | 50 |
| 3 | 3-fluoro-4-methoxyphenyl | SH | 85 |
| 4 | 2,6-dichlorophenyl | SH | 90 |
| 5 | phenyl | $CH_2NH_2$ | 100 |
| 6 | phenyl | $CH_2OH$ | 66 |

Whilst compound No. 6 had good activity at 0.1 mg/kg it was found that the compound was inactive at the higher dose of 1 mg/kg suggesting a bell-shaped dose-response curve.

We claim:

1. A method of treating anxiety and/or cognitive disorders in a host in need thereof which comprises administering an effective amount of a compound of the formula (1):

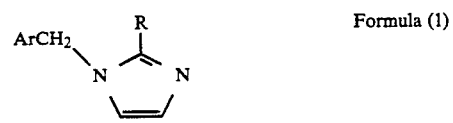

Formula (1)

wherein

Ar is 3,5-difluorophenyl, 2,6-dichlorophenyl, 3,4-dihydroxyphenyl, or 3-fluoro-4-methoxyphenyl and R is SH, or Ar is phenyl and R is $CH_2NH_2$ or $CH_2OH$, or a pharmaceutically acceptable salt thereof.

2. A method according to claim 1 wherein the compound of the formula (1) is 1-benzyl-2-(hydroxymethyl)imidazole.

3. A method according to claim 1 wherein the compound of the formula (1) is 1-benzyl-2-(aminomethyl)imidazole.

* * * * *